United States Patent [19]

Schröder et al.

[11] Patent Number: 5,298,240
[45] Date of Patent: Mar. 29, 1994

[54] HAIR CARE COMPOSITION IN THE FORM OF A MICROEMULSION

[75] Inventors: Friedel Schröder, Darmstadt; Günther Lang, Reinheim, both of Fed. Rep. of Germany

[73] Assignee: Wella Aktiengesellschaft, Darmstadt, Fed. Rep. of Germany

[21] Appl. No.: 9,341

[22] Filed: Jan. 26, 1993

Related U.S. Application Data

[63] Continuation of Ser. No. 791,984, Nov. 14, 1991, abandoned.

[30] Foreign Application Priority Data

Dec. 7, 1990 [DE] Fed. Rep. of Germany ....... 4039063

[51] Int. Cl.$^5$ ............................................. A61K 7/075
[52] U.S. Cl. ......................................... 424/70; 424/71; 424/401
[58] Field of Search ................... 424/70, 71, 401

[56] References Cited

U.S. PATENT DOCUMENTS

| | | |
|---|---|---|
| 3,101,300 | 8/1963 | Siegal et al. ............................ 424/70 |
| 3,192,117 | 6/1965 | Kaiser et al. ............................ 8/405 |
| 3,228,842 | 1/1966 | Markland et al. ...................... 424/70 |
| 4,146,499 | 3/1979 | Rosano ............................. 252/186.32 |
| 4,369,037 | 1/1983 | Matsunaga et al. ................. 8/127.51 |
| 4,472,291 | 9/1984 | Rosano ............................. 252/186.28 |
| 4,777,039 | 10/1988 | Lang et al. ............................ 424/70 |
| 4,835,266 | 5/1989 | Lang et al. ............................ 536/20 |
| 4,975,093 | 12/1990 | Clausen et al. ......................... 8/428 |

OTHER PUBLICATIONS

CFTA Cosmetic Ingredien Handbook, The Cosmetic Toiletry and Fragrance Assoc., Inc., 1988, pp. 12-13 and pp. 31-32.
H. P. Fiedler, Lexikon der Hilfsstoffe für Pharmazie Kosmetik und angrenzende Gebiete: Editio Cantor, 1989, pp. 910-911.
H. Janistyn, Handbuch der Kosmetik und Riechstoffe, Dr. A. Huthig Verlag, 1975, pp. 738-741.

*Primary Examiner*—Thurman K. Page
*Assistant Examiner*—Robert H. Harrison
*Attorney, Agent, or Firm*—Michael J. Striker

[57] ABSTRACT

A hair care composition in the form of a gel-like, highly viscous microemulsion, especially suitable for damaged hair, containing:
a) from 5 to 20 percent by weight of a nonionic surfactants with an HLB-value of from 5 to 12 or mixtures of the nonionic surfactants, the mixtures having HLB-values of from 6 to 10;
b) from 5 to 20 percent by weight of at least one oil;
c) from 0.5 to 10 percent by weight of at least one cationic surfactant; and
d) from 50 to 89.5 percent by weight water, and not containing a nonionic surfactant with an HLB-value of greater than 12.

4 Claims, No Drawings

HAIR CARE COMPOSITION IN THE FORM OF A MICROEMULSION

This application is a continuation of application Ser. No. 07/791,984, filed Nov. 14, 1991, and now abandoned.

BACKGROUND OF THE INVENTION

The present invention relates to a hair care composition in the form of a microemulsion, which contains at least one oil, at least one nonionic surfactant with an HLB value of 5 to 12, at least one quaternary surfactant and water. Furthermore, the invention relates to hair care compositions of this type having a high gel-like high viscosity.

The physical, chemical and morphological properties of hair are negatively influenced by a variety of different actions. Thus the hair structure is damaged by cosmetic treatments, such as repeated bleaching, permanent wave treatments and dyeing, frequent washing of the hair with removal of fats or degreasing, and also by the effects of the environment such as moisture, temperature differences and sunlight. The hair becomes brittle and looses its sheen. The hair damaged in this way collects in combs and brushes electrostatically. The roughened hair surface leads to a poor combability and disentanglability of the hair by formation of knots and tangles. Thus hair care agents having improved combability and hair care properties have a considerable significance.

Hair care composition for improving the condition of the hair, usually in the form of emulsions or suspensions, contain fatty alcohol, waxes, oils and anionic and cationic surfactants.

Hair care compositions are usually turbid fluids or highly viscous preparations.

In the past attempts were made to make clear hair care compositions or hair rinses, for example aqueous solutions of cationic surfactants or cationic polymers were thickened by nonionic polymers. These type of hair care compositions however up to now have been unable to produce the conditioning effects of a cationic emulsion composition.

In contrast to the usually used two or multiphase hair care compositions, which have the added risk of separation and deposition, microemulsions are clear, thermodynamically stable, quasi-one phase system. By "quasi-one phase" we mean that they behave in many ways as if they were a one phase system.

Clear homogeneous microemulsions for topical treatment of skin and hair are known from EP Published Patent Application 0 278 660 from skin and hair, which contain at least 20 percent by weight of a hydrophobic oil phase, 0.01 to 20 percent by weight of a quaternary ammonium surfactant and 0.01 to 20 percent by weight of a hydrophilic phase, which can be water, and a co-surfactant in sufficient quantity. The microemulsions described in the examples of European Published Patent Application 0 278 660 are not hair care agents or compositions and have a comparatively small water content (maximum 6 percent by weight) and a high oil content. The microemulsions described there are barely acceptable as hair care compositions, since they load the hair strongly with oil, and are difficult to rinse out of the hair and give the hair a greasy and stranded appearance.

The microemulsions described in European Published Patent Application 0 278 660 are moreover dilute liquids. This type of dilute liquid consistency is unsuitable for a hair care composition, since these dilute liquid compositions have already dripped away from the hair during the time during which they are supposed to act on the hair.

SUMMARY OF THE INVENTION

It is an object of the present invention to provide a hair care composition in the form of a microemulsion, which does not load the hair with oil because of its high oil content and has a gel-like high viscosity, which prevents the dripping away of the hair care composition before it has time to act.

It is also an object of the present invention to provide a hair care composition of the above type in the form of a microemulsion, which also guarantees a good conditioning and a good wet and dry combability of the hair as well as good hair feel and hair gloss.

According to the invention, the hair care microemulsion composition contains:

a) from 5 to 20 percent by weight of a nonionic surfactant with an HLB-value of from 5 to 12 or a mixture of these surfactants, the HLB-value of the surfactant mixture amounting to from 6 to 10;

b) 5 to 20 percent by weight of at least one oil;

c) 0.5 to 10 percent by weight of at least one cationic surfactant; and d) 50 to 89.5 percent by weight water. Furthermore the microemulsion composition contains no nonionic surfactant with an HLB-value greater than 12, which fulfills the objects of the invention in an outstanding way.

The hair care composition of the invention is very easily worked into the hair, does not drip away too quickly because of its highly viscous consistency and causes an outstanding improvement of the wet and dry combability of the hair and an improved feel, particularly of damaged hair. Furthermore, hair treated with this hair care agent has an outstanding gloss. The hair care composition has also an optically clear, homogeneous gel-like highly viscous consistency.

In contrast to the dilute liquid microemulsions described in European Published Patent Application 0 278 660, especially those described in Examples 5 and 8 of European Published Patent Application 0 278 660, which have flow properties of a Newtonian liquid (Haake Rotation viscometer RV 12, Measuring Section 500, Measurement System NV, 20° C.), the gel-like highly viscous hair care compositions of the invention has flow properties of a plastic mass. The typical flow limit for the flow behavior of a plastic mass is, for example for the hair care composition according to example 15 of this application, at 146 Pascal (Haake Rotation Viscometer RV 12, Measuring Section 500, Measuring System PKV-0.5, 20° C.).

Under hair care compositions in the present invention are understood agents, which act on the hair for only a short time, for example from 2 to 5 minutes, so-called rinses or conditioners, which act on hair for somewhat longer time intervals, e.g. from 5 to 30 minutes and are usually called hair treatment compositions or treatment packages.

The hair care compositions described here should contain only nonionic surfactants with an HLB-value of from 5 to 12, however advantageously also HLB-values of from 6 to 10. The hair care composition according to the invention contains a mixture of several nonionic surfactants, which have an HLB-value of from 5 to 12, advantageously however an HLB-value of from 6 to 10, so that the HLB-value of the surfactant mixture amounts to from about 6 to 10. It is understood that under the HLB-values the values for hydrophilic-lipophilic balance in this application are as defined in Reference books, for example, in G.Nowak, The Cosmetic Preparations, Vols. 2,3, 1984 Edition, pp. 174 to 177.

For the nonionic surfactants suitable for use in the hair care composition according to the invention, the following are suitable: $C_{12}$ to $C_{18}$ fatty alcohols ethoxylated with from 1 to 6, advantageously from 2 to 5, ethylene oxide units, for example, Lauryl-, Cetyl-, Oleyl- or Stearyl- alcohols ethoxylated with from 2 to 5 Mol ethylene oxide per Mol fatty alcohol; polyglyceryl ethers of saturated and unsaturated $C_{12}$ to $C_{18}$ fatty acids with 1 to 5, advantageously 1 to 3, glyceryl groups in a molecule; glycerides of $C_{12}$ to $C_{18}$ fatty a with 1 to 5, advantageously 1 to 3, glyceryl groups, e.g. glycerin monolaurate, diglyceryl monolaurate, triglyceryl monolaurate, glycerin monomyristate or trigylceryl monoisostearate; Sorbitan fatty acid esters of $C_{12}$ to $C_{18}$ fatty acids/ethoxylated with from 1 to 6 ethylene oxide units and $C_{12}$ to $C_{18}$ fatty acid glycosides with 1 to 3 sugar groups, for example glucose groups.

The nonionic surfactants or surfactant mixture is contained in the hair care composition according to the invention in an amount of 5 to 20 percent by weight, advantageously 8 to 15 percent by weight.

Natural or synthetic oils or mixtures of natural and synthetic oils can be used as the oil in the hair care composition according to the invention. Of the natural or synthetic oils which can be used in the hair care composition according to the invention, the following can be mentioned: paraffin oil, linear chain fatty acid esters, for example, Myristyl myristinate, Lauric acid hexylester or Oleic acid oleyl ester; branched fatty acid esters such as isononoic acid cetyl or stearyl ester; isooctyl fatty acid esters, such as isooctyl stearate; silicone oil, for example octamethyl tetracyclosiloxane; Squalene and vegetable oils, for example Jojoba Oil.

The hair care composition according to the invention contains from 5 to 20 weight percent, advantageously 11 to 19 percent at least of one oil.

All cationic surfactants suitable for use in cosmetic preparations can be used in the compositions according to the invention. These cationic surfactants include quaternary alkylammonium compounds. A suitable surfactants the following can be mentioned: benzyldialkylammonium chlorides or bromides, e.g. benzyldimethylstearylammonium chlorides; alkyltrimethyl ammonium salts, e.g. Cetyltrimethylammonium chlorides or bromides; alkyldimethylhydroxyethylammonium chlorides or bromides; dialkyldimethylammonium chlorides or bromides; alkylamidoethyl trimethylammonium ether sulfates; alkylpyridinium salts, e.g. Lauryl- or Cetylpyridinium chlorides; imidazoline compounds derivatives and compounds with cationic character, such as amine oxides, for example, alkyldimethyl amine oxides or alkylaminoethyldimethyl amine oxides.

The hair care composition according to our invention contains 0.5 to 10 percent by weight, advantageously 1.5 to 6 percent by weight, of at least one cationic surfactant.

The water content of the hair care composition according to our invention amounts to from 50 to 89.5 percent by weight, advantageously 60 to 80 percent by weight.

Understandably based on the clear hair compositions according to the invention also turbid or pearlescent turbid hair care compositions can be made, since a turbidity-producing agent can be added in an amount of from 0.5 to 5 weight percent, for example, ethyl glycol distearate, or a pearlescence producing agent in the amount of from 1.0 to 10.0 percent by weight, for example, a mixture of fatty acid monoalkylol amide and ethylene glycol distearate.

The hair care compositions described here can be altered in their appearance by addition of solids such as metal flakes, finely divided silicon dioxide or water insoluble antidandruff agents, for example Zinc pyrithione.

Understandably the hair care composition according to the invention can include additional standard cosmetic additives besides the components mentioned above, for example: perfume oils in an amount of from 0.5 to 5.0 percent by weight; thickeners, for example coconut fatty acid diethanol amide, in an amount of 0.5 to 10.0 percent by weight; thinning agents, for example, 1,2 propylene glycol or ethyoxylated Sorbitan monolaurate, in an amount of from 0.5 to 5.0 percent by weight; buffer substance, for example, sodium citrate or sodium phosphate, in an amount of from 0.1 to 1.0 percent by weight; hair conditioning additives, for example fatty acids, fatty alcohols, protein-partial hydrolysates, modified natural or synthetic, advantageously cationic, polymers, such as Cellulose derivatives, cationic Cellulose derivatives, Chitosan and cationic Chitosan derivatives; Care materials, for example, Lanolin derivatives, Cholestrol and Pantothenic acid in an amount of from 0.1 to 10 percent by weight; and physiologically acceptable inorganic salts, e.g. sodium chloride; further moisturizing agents; light damage-preventing agents, bactericidal and fungicidal compounds; dye compounds; antioxidants for example ascorbic acids and reducing compounds, for example glyoxylic acid; complexing agents; antifat- and antidandruff agents.

For the simultaneous tinting of the hair in one particular embodiment of the hair care composition of the invention the hair care composition contains 0.05 to 2.0 percent by weight of at lest one dye acting directly on the hair, for example a direct dye selected from the following Classes of dyes: aromatic nitrodyes, e.g. 1,4-diamino-2-nitrobenzene; azodyes, e.g. Acid Brown 4 (C.I. 14 804); anthraquinone dyes, e.g. Disperse Violet 4 (C.I. 61 105);and Triphenylmethane dyes, for example Basic Violet 1 (C.I. 42 535); wherein the dyes of this type can have substituents of an acidic, nonionic or basic character.

The hair care composition according to the invention can be made by first mixing an aqueous solution of cationic surfactants heated to from 60° to 70° C. into a solution of nonionic surfactants in oil at about the same temperature with stirring. On cooling the hair care composition according to the invention sets into a clear gel. With suitable selection of components it is also possible without previous heating to homogenize the liquid mixture of the oil phase and the nonionic surfactants in a suitable mixing device to avoid inclusion of air with the aqueous solution of cationic surfactants.

The hair care composition according to the invention, is distributed in an amount of from about 10 to 30 g, usually after washing the hair, in the hand towel dried hair according to the feel of the hair. After an acting time of about 1 to 30 minutes, advantageously 3 to 15 minutes, the hair is rinsed and then dried.

The acting time of the hair care composition within the previously mentioned time limits depends on the application purpose. If the purpose is simply a rinsing of the hair, then from 1 to 5 minutes is sufficient. If the purpose is hair care, then from 3 to 15 minutes should be allowed for the composition to act on the hair. However if the hair is to be simultaneously tinted then an acting time of from 10 to 30 minutes is necessary.

The hair care composition according to the invention distributed in the prewashed dried hair can be rinsed again from the hair without problems after the acting time.

The hair care composition according to the invention has an exceptionally outstanding wet and dry combability, a pleasant feel and a pleasing gloss in the dried state.

The hair care composition is now illustrated by the following Examples, which should not be considered as limiting the claims appended hereinbelow.

EXAMPLES

| Hair Care Composition | | |
|---|---|---|
| Example 1 | | |
| 11.25 | g | Paraffin oil |
| 5.50 | g | Tetraoxyethylene lauryl ether |
| 4.50 | g | Glyceryl monolaurate |
| 1.88 | g | Cetyltrimethylammonium chloride |
| 76.78 | g | Water, completely desalenated. |
| 100. | g | |
| Example 2 | | |
| 8.40 | g | Tetraoxyethylene lauryl ether |
| 7.50 | g | Oleic acid oleyl ester |
| 6.00 | g | Paraffin oil |
| 3.60 | g | Glyceryl monolaurate |
| 2.25 | g | Cetyltrimethylammonium chloride |
| 72.25 | g | Water, desalenated |
| 100. | g | |
| Example 3 | | |
| 13.50 | g | Mixture of Cetyl- and Stearyl- esters of isononoic acid |
| 7.80 | g | Tetraoxyethylene lauryl ether |
| 4.20 | g | Glyceryl monolaurate |
| 2.25 | g | Cetyltrimethylammonium chloride |
| 72.25 | g | Water, completely desalenated |
| 100. | g | |
| Example 4 | | |
| 13.50 | g | Octamethylcyclotetrasiloxane |
| 12.00 | g | Trioxyethylene lauryl ether |
| 2.25 | g | Cetyltrimethylammonium chloride |
| 72.25 | g | Water, completely desalenated |
| 100. | g | |
| Example 5 | | |
| 13.50 | g | Isooctyl stearate |
| 8.40 | g | Tetraoxyethylene lauryl ether |
| 3.60 | g | Glyceryl monolaurate |
| 72.25 | g | Cetyltrimethylammonium chloride |
| 2.25 | g | Water, completely desalenated |
| 100 | g | |
| Example 6 | | |
| 12.25 | g | Squalene |
| 4.50 | g | Glyceryl monolaurate |
| 3.50 | g | Tetraoxyethylene lauryl ether |
| 1.88 | g | Cetyltrimethylammonium chloride |
| 77.87 | g | Water, completely desalenated |
| 100 | g | |
| Example 7 | | |
| 11.25 | g | Lauric acid hexyl ester |
| 7.00 | g | Tetraoxyethylene lauryl ether |
| 3.00 | g | Glyceryl monolaurate |
| 1.88 | g | Cetyltrimethylammonium chloride |
| 76.87 | g | Water, completely desalenated |
| 100. | g | |
| Example 8 | | |
| 9.00 | g | Paraffin oil |
| 9.00 | g | Tetraoxyethylene lauryl ether |
| 4.50 | g | 9-octadecenoyl-13-docosenoate |
| 3.00 | g | Glyceryl monolaurate |
| 72.25 | g | Cetyltrimethylammonium chloride |
| 2.25 | g | water, completely desalenated |
| 100 | g | |
| Example 9 | | |
| 13.50 | g | Paraffin oil |
| 6.05 | g | Tetraoxyethylene lauryl ether |
| 4.95 | g | Glyceryl monolaurate |
| 3.78 | g | Cetyldimethylbenzylammonium chloride |
| 71.72 | g | Water, completely desalenated |
| 100. | g | |
| Example 10 | | |
| 11.25 | g | Paraffin Oil |
| 5.50 | g | Tetraoxyethylene lauryl ether |
| 4.50 | g | Glycerylmonolaurate |
| 2.48 | g | Cetyldimethyl-2-hydroxyethyl ammonium dihydrogen phosphate |
| 76.27 | g | Water, completely desalenated |
| 100 | g | |
| Example 11 | | |
| 13.50 | g | Paraffin Oil |
| 8.00 | g | Diglyceryl monolaurate |
| 4.00 | g | Glyceryl monolaurate |
| 2.25 | g | Cetyltrimethylammonium chloride |
| 72.25 | g | Water, completely desalenated |
| 100 | g | |
| Example 12 | | |
| 13.50 | g | Paraffin Oil |
| 6.00 | g | Glyceryl monolaurate |
| 6.00 | g | Triglyceryl monoisostearate |
| 72.25 | g | Cetyltrimethylammonium chloride |
| 2.25 | g | Water, completely desalenated |
| 100 | g | |
| Example 13 | | |
| 13.50 | g | Paraffin Oil |
| 7.00 | g | Glyceryl monolaurate |
| 5.00 | g | Triglyceryl monoisostearate |
| 72.25 | g | Cetyltrimethylammonium chloride |
| 2.25 | g | Water, completely desalenated |
| 100 | g | |
| Example 14 | | |
| 15.00 | g | Paraffin Oil |
| 7.50 | g | Stearate ester of Sorbitol and of Sorbitol anhydride, ethoxylated with 4 Mol ethylene oxide |
| 7.00 | g | Dioxyethylene lauryl ether |
| 2.85 | g | Cetyltrimethylammonium chloride |
| 67.65 | g | Water, completely desalenated |
| 100. | g | |
| Example 15 | | |
| 11.25 | g | Paraffin oil |
| 5.50 | g | Tetraoxyethylene lauryl ether |
| 4.50 | g | Glyceryl monolaurate |
| 1.875 | g | Trimethylhexadecylammonium chloride |
| 76.875 | g | Water, completely desalenated |
| 100. | g | |
| Example 16 | | |
| 15.75 | g | Paraffin oil |
| 12.75 | g | Pentaoxyethylene oleylether |
| 1.75 | g | Trimethylhexadecylammonium chloride |
| 1.50 | g | Tetraoxyethylene lauryl ether |
| 1.00 | g | Perfume oil |
| 0.20 | g | Citric Acid |
| 67.05 | g | Water, completely desalenated |
| 100. | g | |

Method of Hair Treatment

About 20 g of hair care composition of Examples 1 to 16 are distributed in the prewashed, hand towel-dried hair. After acting on the hair for about 3 to 15 minutes the hair is rinsed and then dried. As a result the hair is provided with an outstanding combability, a very good feel and a pleasing gloss.

Percentages in the specification and claims are given in percent by weight.

While the invention has been illustrated and described as embodied in a hair care composition in the form of a microemulsion, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. A hair care composition in the form of a microemulsion consisting essentially of:
    a) from 5 to 20 percent by weight of a nonionic surfactant selected from the group consisting of $C_{12}$ to $C_{18}$ fatty alcohols ethoxylated from 1 to 6 ethylene oxide groups; polyglyceryl ethers of saturated and unsaturated $C_{12}$ to $C_{18}$ fatty acids with 1 to 5 glyceryl groups; glycerides of $C_{12}$ to $C_{18}$ fatty acids with 1 to 5 glyceryl groups; Sorbitan fatty acid esters of $C_{12}$ to $C_{18}$ fatty acids; $C_{12}$ to $C_{18}$ fatty acids glycosides with 1 to 3 sugar groups; and mixtures thereof;
    b) from 11 to 19 percent by weight of at least one oil selected from the group consisting of paraffin oils, straight chain and branched chain fatty acid esters, silicone oil, squalene and vegetable oils;
    c) from 1.5 to 6 percent by weight of at least one cationic surfactant selected from the group consisting of benzyldialkylammonium chlorides, benzyldialkylammonium bromides; alkyltrimethylammonium salts; alkyldimethylhydroxyethylammonium chlorides, alkyldimethylhydroxyethylammonium bromides; dialkyldimethylammonium chlorides, dialkyldimethylammonium bromides; alkylamidethialtrimethylammonium ether sulfates; alkylpyridinium salts; imidazoline compounds and amine oxides; and
    d) from 60 to 80 percent by weight water, and not containing one of said nonionic surfactants with an HLB-value of greater than 12.

2. A hair care composition as defined in claim 1, wherein said straight chain and branched chain fatty acid esters comprise isooctyl fatty acid esters.

3. A hair care composition in the form of a microemulsion consisting of:
    a) from 5 to 20 percent by weight of a nonionic surfactant selected from the group consisting of $C_{12}$ to $C_{18}$ fatty alcohols ethoxylated from 1 to 6 ethylene oxide groups; polyglyceryl ethers of saturated and unsaturated $C_{12}$ to $C_{18}$ fatty acids with 1 to 5 glyceryl groups; glycerides of $C_{12}$ to $C_{18}$ fatty acids with 1 to 5 glyceryl groups; Sorbitan fatty acid esters of $C_{12}$ to $C_{18}$ fatty acids; $C_{12}$ to $C_{18}$ fatty acids glycosides with 1 to 3 sugar groups; and mixtures thereof;
    b) from 11 to 19 percent by weight of at least one oil selected from the group consisting of paraffin oils, straight chain and branched chain fatty acid esters, silicone oil, squalene and vegetable oils;
    c) from 1.5 to 6 percent by weight of at least one cationic surfactant selected from the group consisting of benzyldialkylammonium chlorides, benzyldialkylammonium bromides; alkyltrimethylammonium salts; alkyldimethylhydroxyethylammonium chlorides, alkyldimethylhydroxyethylammonium bromides; dialkyldimethylammonium chlorides, dialkyldimethylammonium bromides; alkylamidethialtrimethylammonium ether sulfates; alkylpyridinium salts; imidazoline compoundsand amine oxides; and
    d) from 60 to 80 percent by weight water; and
    e) 0.05 to 2.0 percent by weight of at least one direct dye for simultaneous tinting of the hair, and not containing one of said nonionic surfactants with an HLB-value of greater than 12.

4. A hair care composition as defined in claim 3, wherein said straight chain and branched chain fatty acid esters comprise isooctyl fatty acid esters.

* * * * *